July 1, 1969 D. L. ARMSTRONG Plant Pat. 2,900
ROSE PLANT
Filed Dec. 13, 1967
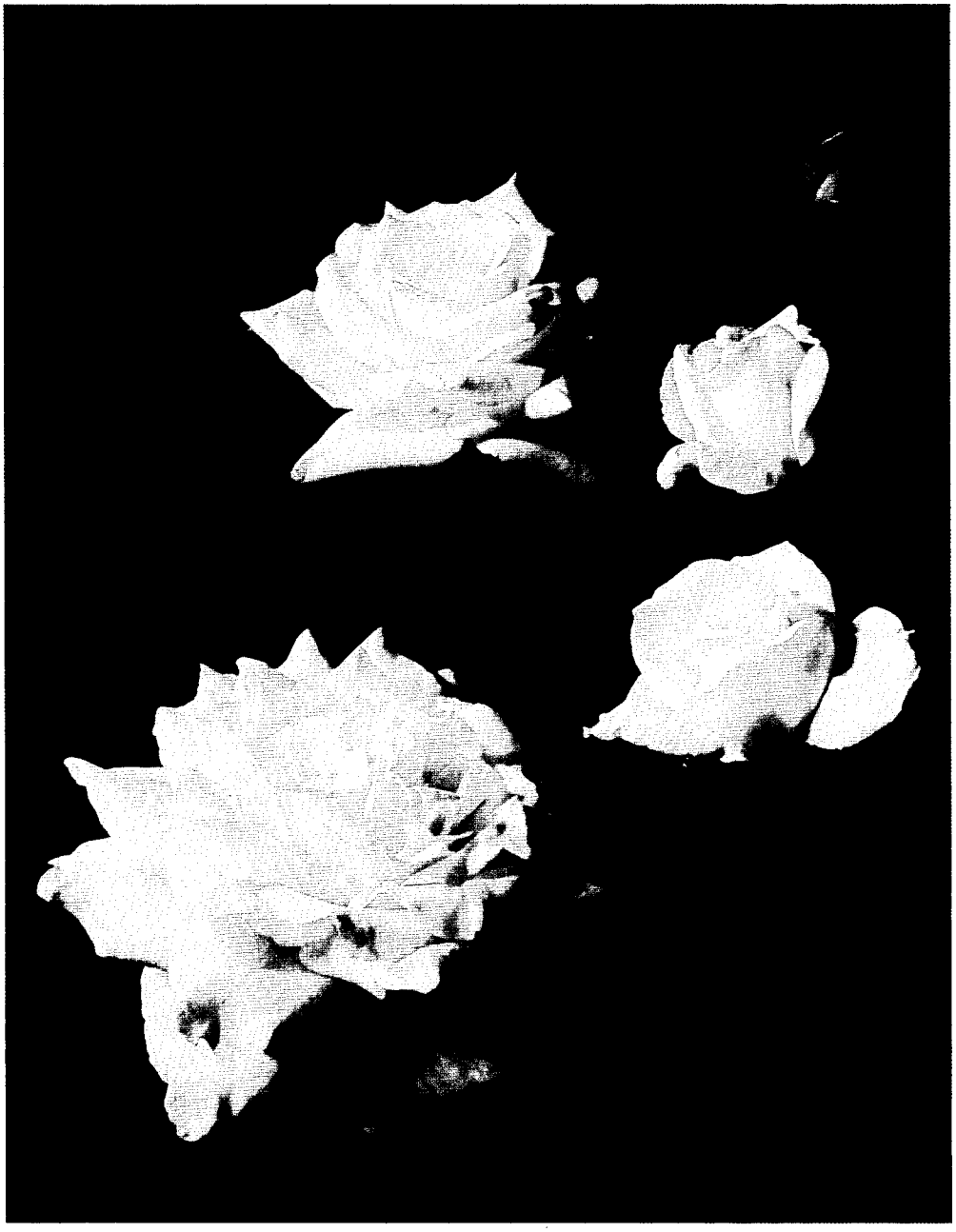
Inventor.
D. L. Armstrong
By: Robb & Robb
Attorneys.

United States Patent Office

Plant Pat. 2,900
Patented July 1, 1969

2,900
ROSE PLANT

David L. Armstrong, Ontario, Calif., assignor to Armstrong Nurseries, Inc., Ontario, Calif., a corporation of California

Filed Dec. 13, 1967, Ser. No. 690,364
Int. Cl. A01h *5/02*
U.S. Cl. Plt.—15 1 Claim

The present invention relates to a new and distinct variety of rose plant of the hybrid tea class, which was originated by me by crossing the rose variety known as "Helen Traubel" (Plant Patent No. 1,028) with the rose variety known as "Tiffany" (Plant Patent No. 1,304), the former being the seed parent and the latter being the pollen parent.

The new variety resulted from an extensive breeding program conducted by me and having for its objective to produce improved hybrid rose varieties bearing flowers in the pink and pink-and-yellow-blend color range, and combining the large flower size and superior bud and open flower form that is characteristic of the parent varieties. This variety is one of the achievements of the objective, as evidenced by the following unique combination of characteristics which are outstanding in the new variety and which distinguish it from its parents, as well as from all other varieties of which I am aware:

(1) A vigorous, bushy, attractive plant of rounded and upright to spreading habit;

(2) A habit of usually bearing its flowers singly on medium to long stems of good strength;

(3) Attractive, quite double, medium to large flowers of excellent urn-shaped bud form and graceful open-flower form, combining the best of these aspects of the parent varieties; and (4) A distinctive, attractive and clear light yellow flower color.

In comparison with its seed parent "Helen Traubel," the new variety has a more bushy and compact plant habit; greater flower petalage; and a light yellow flower color instead of the apricot-pink flower color of this parent.

As compared with its pollen parent "Tiffany," the new variety primarily differs by having a light yellow flower color instead of the pink or pink-and-yellow blended flower color of this parent.

Asexual reproduction of my new variety by budding, as performed at Ontario, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Bush; outdoor; seedling; for cut flowers and/or garden decoration.
Class: Hybrid tea.
Breeding: Seedling.
*Seed parent.*—"Helen Traubel."
*Pollen parent.*—"Tiffany."
Propagation: Holds its distinguishing characteristics through succeeding propagations by budding.

*Flower*

Locality where grown and observed: Ontario, Calif.
Flowers borne: Usually singly, but sometimes three or four to stem; in irregular clusters; on medium to long stems of normal strength.
Quantity of bloom: Abundant, outdoors.
Continuity: Nearly continuous during growing season.
Fragrance: Moderate.
Bud:
*Peduncle.*—Average length; average caliper; usually smooth; with several to many stipitate glands and several to many small prickles. Color—near Apple Green, Plate XVII (R).
*Before calyx breaks.*—Size—medium. Form—medium length; ovoid.
*As calyx breaks.*—Color—between Uranium Green, Plate 63/3, page 63 (W) and Dresden Yellow, Plate 64/3, page 64 (W).
*Sepals.*—Usually with foliaceous appendages extending ¼ to ½ of sepal length. Inner surface—with fine, wooly tomentum. Outer surface—usually smooth, but sometimes with few small stipitate glands. Alternate margins—lined with fine, wooly tomentum. Other margins—with several to many small stipitate glands and small, slender foliaceous parts.
*As first petal opens.*—Size—average. Form—medium length; ovoid; usually urn-shaped. Color: outside—near Primrose Yellow, Plate 601/3, page 65 (W), bending with near Primrose Yellow, Plate 601/1, page 65 (W) toward base of petal; inside—near Mimosa Yellow, Plate 602/3, page 143 (W), blending with near Mimosa Yellow, Plate 602/1, page 143 (W) toward base of petals.
*Opening.*—Opens up well; is not retarded or prevented from opening by cold, hot, wet or dry weather.
Bloom:
*Size (when fully open).*—From average to large; from 4 inches to 5 inches.
*Petalage.*—Double; from 50 to 55 petals; plus 8 to 10 petaloids; arranged irregularly.
*Form.*—High-centered at first, but becoming cupped to high-centered; petals being at first tightly cupped, with tips reflexed outward, but later becoming more loosely flat to cupped at maturity, with tips reflexed outward; outside petals of newly opened flower usually reflexed outward both along edges and apex of petal, and intermediate petals of newly opened flower usually reflexed slightly outward along apex of petal; outside and intermediate petals of 3-days open flowers usually reflexed outward both along edges and apex of petals.
Petals:
*Texture.*—Medium thickness.
*Appearance.*—Inside—satiny. Outside—satiny.
*Shape.*—Outside—between round and broadly obovate, sometimes with 1 or 2 notches. Intermediate—obovate, with apex rounded and sometimes with 1 or 2 notches. Inside—narrowly obovate, with apex rounded.

This description of a newly opened flower was made from a rose grown outdoors during the month of October at Ontario, Calif.

*Color.*—Outer petal: outside surface—between white and near Primrose Yellow, Plate 601/3, page 65 (W), blending with near Primrose Yellow, Plate 601/3, page 65 (W) toward base of petal; inside surface—same as outside surface. Intermediate petal: outside surface—same as outside surface of outer petal; inside surface—same as inside surface of outer petal. Inner petal: outside surface—near Empire Yellow, Plate 603/1, page 66 (W), blending with near Empire Yellow, Plate 603, page 66 (W) toward base of petal; inside surface—same as outside surface.

This description was made from a rose that was open for three days outdoors during the month of October at Ontario, Calif.

*Color.*—Outer petal: outside surface—between white and near Mimosa Yellow, Plate 602/3, page 143 (W), blending with near Mimosa Yellow, Plate 602/2, page 143 (W) toward base of petal; inside surface—same as outside surface. Inner petal: outside surface—same as outside surface of outer petal; inside surface—same as outside surface.

*General color effect.*—Newly opened flower—between Chinese Yellow, Plate 606/1, page 68 (W) and Empire Yellow, Plate 603/3, page 66 (W). Three days open—between Straw Yellow, Plate 604/2, page 67 (W) and white to near Empire Yellow, Plate 603/3, page 66 (W).

*Behavior.*—Drop off cleanly; not particularly affected by cold, hot, wet or dry weather.

*Flower longevity.*—On bush in garden—3 or 4 days in October. Cut roses grown outdoors and kept at living-room temperatures—3 or 4 days in October.

*Reproductive organs*

Stamens: Average number; arranged regularly about pistils; a few mixed with petaloids.

Filaments: From medium length to long (varying from 6 mm. to 8 mm. long); most with anthers. Color—near Lemon Yellow, Plate 4/1, page 4 (W).

Anthers: Small; all open approximately at once. Color: upper side—margins near Saffron Yellow, Plate 7, page 7 (W), with remainder near Lemon Yellow, Plate 4/2, page 4 (W); under side—margins near Saffron Yellow, Plate 7, page 7 (W), with remainder near Lemon Yellow, Plate 4/2, page 4 (W).

Pollen: From sparce to moderate abundance. Color—near Tangerine Orange, Plate 9/1, page 9 (W).

Pistils: Many (approximately 130 in number).

Styles: Uneven; average length; thin; bunched. Color—upper ¼ of style near Carmine, Plate 21/2, page 21 (W), with remainder near Primrose Yellow, Plate 601/3, page 65 (W).

Stigma: Color—near Yellow Ochre, Plate 07/3, page 101 (W).

Ovaries: Usually all enclosed in calyx.

Hips: None observed.

*Plant*

Foliage:

*Leaves.*—Compound of usually 3–7 leaflets; abundant; medium size; leathery; semi-glossy.

*Leaflets.*—Shape — broadly oval. Apex — acute. Base—round. Margin—simply serrate.

*Color.*—Mature: upper surface—near Forest Green, Plate XVII (R); under surface—near Light Elm Green, Plate XVII (R). Young: upper surface—near Deep Dull Yellow-Green (1), Plate XXXII (R); under surface—near Chromium Green, Plate XXXII (R).

*Rachis (the supporting stem of the compound leaf).*—Average size. Upper side—grooved; with few to several small stipitate glands on edges. Under side—smooth; with none to few small stipitate glands, and none to few small prickles.

*Stipules.*—From short to medium length; narrow; with short to medium length points turning out at an angle of less than 45°.

*Desease resistance.*—Better than average resistance to mildew, as determined by comparison with other varieties grown under the same conditions at Ontario, Calif.

Growth:

*Habit.*—Bushy; upright-spreading; much branched.

*Growth.*—Free.

*Canes.*—Medium caliper.

*Main stems.*—Color—near Light Yellowish-Olive, Plate XXX (R). Large prickles—several; from medium length to long; hooked slightly downward; with medium length, narrow base; color—near Mikado Brown, Plate XXIX (R). Small prickles—very few; color—near Mikado Brown, Plate XXIX (R). Hairs—none.

*Branches.*—Color—near Biscay Green, Plate XVII (R). Large prickles—from few to several; medium length; hooked slightly downward; with medium length, narrow base; color—near Russet, Plate XV (R), Small prickles—very few; color—near Russet, Plate XV (R). Hairs—none.

*New shoots.*—Color—near Apple Green, Plate XVII (R). Large prickles—from short to medium length; hooked slightly downward; with short to medium length, narrow base; color—near Ochre Red, Plate XXVII (R). Small prickles—none. Hairs—none.

I claim:

1. A new and distinct variety of rose plant of the hybrid tea class, substantially as herein shown and described, characterized particularly as to novelty by the unique combination of a vigorous, bushy, attractive plant of rounded and upright to spreading habit, a habit of usually bearing its flowers singly on medium to long stems of good strength, attractive, quite double, medium to large flowers of excellent urn-shaped bud form and graceful open-flower form, combining the best of these aspects of the parent varieties, and a distinctive, attractive and clear light yellow flower color.

No references cited.

ROBERT E. BAGWILL, *Primary Examiner.*